United States Patent [19]
Goodearl et al.

[11] Patent Number: 5,594,114
[45] Date of Patent: Jan. 14, 1997

[54] SCHWANN CELL MITOGENIC FACTOR, ITS PREPARATION AND USE

[75] Inventors: Andrew D. J. Goodearl, Hertfordshire; Paul Stroobant, London; Michael D. Waterfield, Berkshire, all of England

[73] Assignee: Ludwig Institute for Cancer Research, New York, N.Y.

[21] Appl. No.: 311,365

[22] Filed: Sep. 23, 1994

Related U.S. Application Data

[63] Continuation of Ser. No. 931,041, Aug. 17, 1992, abandoned.

[30] Foreign Application Priority Data

Aug. 14, 1992 [GB] United Kingdom .................. 92 17316

[51] Int. Cl.$^6$ ............................................. C07K 14/475
[52] U.S. Cl. ............................................................. 530/399
[58] Field of Search .................................... 530/350, 399, 530/300

[56] References Cited

U.S. PATENT DOCUMENTS

| | | | |
|---|---|---|---|
| 4,935,341 | 6/1990 | Barbmann et al. ........................ | 435/6 |
| 4,968,603 | 11/1990 | Slamon et al. ............................. | 435/6 |

FOREIGN PATENT DOCUMENTS

| | | |
|---|---|---|
| WO8906692 | 7/1989 | WIPO . |
| WO9014357 | 11/1990 | WIPO . |
| WO9115230 | 10/1991 | WIPO . |
| WO9118921 | 12/1991 | WIPO . |
| WO9212174 | 7/1992 | WIPO . |
| WO9218627 | 10/1992 | WIPO . |
| WO9220798 | 11/1992 | WIPO . |

OTHER PUBLICATIONS

Huang et al., "Purification and Characterization of the neu/erb B2 Ligand–Growth Factor from Bovine Kidney", J. Biol. Chem. 257:11508 (1992).
Lupu et al., "Characterization of a growth factor that binds exclusively to the erbB–2 receptor and induces cellular responses", PNAS USA 89:2287 (1992).
Holmes et al., "Identification of Heregulin, a Specific Activator of p185$^{2rbB2}$" Science 256: 1204 (1992).
Dobashi et al., "Characterization of a neu/c–erbB–2 protein-specific activating factor", P.N.A.S. U.S.A. 88:8582 (1991).
Tarakovsky et al., "KDa polypeptide is theligand for p185neu and is secreted by activated macrophages", Oncogene 6: 2187 (1991).
David et al., "Isolation and characterization of a neu protein-specific activating factor from human ATL–2 cell conditioned medium", Biochem. Biophys. Research Communications, 179: 1536 (1991).
Peles et al., "Isolation of the Neu/HER–2 Stimulatory Ligand: a 44 kd Glycoprotein that Induces Differentiation of Mammary Tumor Cells", Cell 69: 205 (1990).
Lupu et al., "Direct Interaction of a Ligand for the erbB2 Oncogene Product with the EGF Receptor and p185$^{erbB2}$", Science 249: 1552 (1990).
Yarden et al., "Biochemical Analysis of the Ligand for the neu Oncogenic Receptor", Biochemistry 30: 3543 (1990).
Lemke et al., "Identification and Purification of Glial Growth Factor$^1$", J. Neuroscience, vol. 4, No. 1, pp. 75–83, 1984.
Brockes "Assay and Isolation of Glial Growth Factor from the Bovine Pituitary", Methods in Enzymology, 147: 217–225 (1987).
Davis et al., "Platelet–derived Growth Factirs ahd Fibroblast Growth Factors are Mitogens for Rat Schwann Cells", J. Cell Biology, 110: 1353 (1990).
Brokes, "Purification and Preliminary Characterization of A Glial Growth Factor from the Bovine Pituitary", J. Bio. Chem. 255: 18, pp. 8374–8377 (1980).
Brokes et al., "The neuron as a source of mitogen: its influence on the proliferation of glial and non–neural cells", In Development in the Nervous System, Garrod and Feldman eds. pp. 309–327 (1980).
Lemke et al., "An Immunochemical Approach to the Purification and Characterization of Glial Growth Factor", Monoclonal Antibodies to Neural Antigens, McKay, Raff and Reichardt, eds, pp. 133–140 (1981).
Wen et al., "Neu Differentiation Factor: A Transmembrane Glycoprotein containing an EGF Domain and an Immunoglobulin Homology Unit", Cell 69: 559 (1992).
Marchionni et al (1993) Mature, 362:312.
Goodearl et al 1992 J Cell Biochem, Suppl O (16pt7):79.
Brockes et al 1980 J. Biol. Chem 255(18):8374.
Brockes 1987 Methods Enz 147:217.

*Primary Examiner*—Robert A. Wax
*Assistant Examiner*—K. Cochrane Carlson
*Attorney, Agent, or Firm*—Felfe & Lynch

[57] ABSTRACT

The invention provides a new Schwann cell-mitogenic factor of molecular weight about 43 to 45 kilodaltons, when isolated by SDS-PAGE. The invention provides therapeutic formulation comprising the new factor, and the use of the factor and the said formulations in treating conditions which involve a factor-sensitive or factor-responsive cell type.

1 Claim, 7 Drawing Sheets

SCHWANN CELL MITOGENIC FACTOR, ITS PREPARATION AND USE

This Application is a continuation of application Ser. No. 07/931,041, filed Aug. 17, 1992, now abandoned.

This invention relates to a new polypeptide material found in vertebrate species, which polypeptide is a mitogenic growth factor, e.g. having activity on cultured Schwann cells. The invention is also concerned, inter alia, with a novel isolation process capable of producing the factor, and the therapeutic application of the factor. The invention further includes useful peptides characteristic of the factor.

The glial cells of vertebrates constitute the specialized connective tissue of the central and peripheral nervous systems. Important glial cells include Schwann cells which provide myelin sheathing around the axons of neurones, thereby forming individual nerve fibres. Schwann cells provide a sheath effect by forming concentric layers of membrane around adjacent neurone axons, twisting as they develop around the axons. These myelin sheaths are a susceptible element of many nerve fibres, and damage to Schwann cells, or failure in growth and development, can be associated with significant demyelination or nerve degeneration characteristic of a number of peripheral nervous system diseases and disorders. In the development of the nervous system, it has become apparent that cells require various factors to regulate their division and growth, and various such factors have been identified in recent years, including some found to have an effect on Schwann cell division or development.

Thus, Brockes et al., inter alia, in J. Neuroscience, 4 (1984), No 1, 75–83 describe a protein growth factor present in extracts from bovine brain and pituitary tissue, which was named Glial Growth Factor (GGF). This factor stimulated cultured rat Schwann cells to divide against a background medium containing ten percent foetal calf serum. The factor was also described as having a molecular weight of 31,000 and as readily dimerizing. In Meth. Enz., 147 (1987), 217–225, Brockes describes a Schwann cell-based assay for the factor, and emphasises that in purification of the factor the use of reversed-phase HPLC using trifluoroacetic acid as an ion pairing agent must be avoided if biological activity is to be retained.

The J. Neuroscience article of Brockes et al., supra, describes methods of purification of GGF to apparent homogeneity. In brief, one large-scale purification method described involves extraction of the lyophilized bovine anterior lobes and chromatography of material obtained thereby using NaCl gradient elution from CM-cellulose. Gel filtration is then carried out with an Ultrogel column, followed by elution from a phosphocellulose column, and finally, small-scale SDS gel electrophoresis. Alternatively, the CM-cellulose material was applied directly to a phosphocellulose column, fractions from the column were pooled and purified by preparative native gel electrophoresis, followed by a final SDS gel electrophoresis.

Brockes et al. observe that in previously reported gel filtration experiments (Brockes et al., J. Biol. Chem. 255 (1980) 8374–8377), the major peak of growth factor activity was observed to migrate with a molecular weight of 56,000, whereas in the first of the above-described procedures activity was predominantly observed at molecular weight 31,000. It is reported that the GGF dimer is largely removed as a result of the gradient elution from CM-cellulose in this procedure.

In PNAS, 82 (1985), 3930–3934, Benveniste et al. describe a T lymphocyte-derived glial cell growth promoting factor. This factor, under reducing conditions, exhibits a change in apparent molecular weight on SDS gels. In Nature, 348 (1990), 257–260, Kimura et al. describe a factor they term Schwannoma-derived growth factor (SDGF) obtained from a sciatic nerve sheath tumour. The authors state that SDGF does not stimulate the incorporation of tritium-labelled TdR into cultured Schwann cells under conditions where, in contrast, partially purified pituitary fraction containing GGF is active. SDGF has an apparent molecular weight of between 31,000 and 35,000.

In J. Cell. Biol., 110 (1990), 1353–1360, Davis and Stroobant describe the screening of a number of candidate mitogens. Rat Schwann cells were used, the chosen candidate substances being examined for their ability to stimulate DNA synthesis in the Schwann cells in the present of 10% FCS (foetal calf serum), with and without forskolin. One of the factors tested was GGF-carboxymethyl cellulose fraction (GGF-CM), which was mitogenic in the presence of FCS, with and without forskolin. The work revealed that in the presence of forskolin, inter alia, platelet derived growth factor (PDGF) was a potent mitogen for Schwann cells, PDGF having previously been thought to have no effect on Schwann cells.

Holmes et al. Science (1992) 256: 1205 and Wen et al. Cell (1992) 69:559 demonstrate that DNA sequences which encode proteins binding to a receptor ($p185^{erbB2}$) are associated with several human tumors.

The $p185^{erbB2}$ protein is a 185 kilodalton membrane spanning protein with tyrosine kinase activity. The protein is encoded by the erbB2 proto-oncogene (Yarden and Ullrich Ann. Rev. Biochem. 57: 443 (1988)). The erbB2 gene, also referred to as HER-2 (in human cells) and neu (in rat cells), is closely related to the receptor for epidermal growth factor (EGF). Recent evidence indicates that proteins which interact with (and activate the kinase of) $p185^{erbB2}$ induce proliferation in the cells bearing $p185^{erbB2}$ (Holmes et al. Science 256: 1205 (1992); Dobashi et al. Proc. Natl. Acad. Sci. 88: 8582 (1991); Lupu et al. Proc. Natl. Acad. Sci. 89: 2287 (1992)). Furthermore, it is evident that the gene encoding $p185^{erbB2}$ binding proteins produces a number of variably-sized, differentially-spliced RNA transcripts that give rise to a series of proteins, which are of different lengths and contain some common peptide sequences and some unique peptide sequences. This is supported by the differentially-spliced RNA transcripts recoverable from human breast cancer (MDA-MB-231) (Holmes et al. Science 256: 1205 (1992)). Further support derives from the wide range of proteins which act as ligands for the $p185^{erbB2}$ receptor.

One aspect of the present invention is a new glial growth factor which is distinguished from known factors, including those mentioned above, and which is mitogenic for Schwann cells. The invention also encompasses processes for the preparation of this factor, and therapeutic applications of the factor.

Thus, an important aspect of the invention is a polypeptide factor having mitogenic activity stimulating the division of Schwann cells, exhibiting a molecular weight of from about 43 kD to about 45 kD when carrying native glycosylation, and including within its amino acid sequence any one or more of the following peptide sequences:

Lys-Ile-Ser-Lys-Pro-Asp-Leu-Lys-Pro-Phe-Thr-X-Glu-Val-X-(Lys)

Leu-Leu-Gin-Ala-Gln-Gly-Val-Glu-Val-Pro-Ser-Lys-Asp-Ser

Ala-Ser-Glu-Tyr-Ala-Phe-Phe-Glu-Gln-Thr-X-Arg-Glu

Ala-Pro-Pro-Ser-Ala-Phe-Phe-Leu-Phe
Tyr-Glu-Lys-Asp-Ile-Ala-Ala-Tyr-Lys
Lys-Pro-Arg-Asp-Ser-Gln-Ala-Gln-Tyr-Ala-Ala-Glu-Lys
Leu-Leu-Glu-Met-Ala- X-Glu-Val-Lys
Ile-Lys-Gly-Glu-His-Pro-Gly-Leu-Ser-Ile-Gly-Asp-Val-Ala-Lys
(Lys)-Leu-Ala-Thr-Gly-Ala-Val-Pro-Ala-Ser-Leu-Lys;
or any one or more of the following peptide sequences:

Lys-Ser-Glu-Leu-Arg-Ile-Ser-Lys

Lys-Leu-Gly-Asn-Asp-Ser-Ala-Ser-Ala-Asn-Ile-Thr-Ile-Val

Lys-Ala-Ser-Leu-Ala-Asp-Ser-Gly-Glu-Tyr-Met-X-Lys

Lys-Trp-Phe-Lys

Lys-Asp-Leu-Ser-Asn-Pro-Ser-Arg-Tyr-Leu-X-Lys wherein X is an unassigned residue.

The novel peptide sequences set out in the above definition are also aspects of this invention in their own right. These sequences are useful, inter alia, as probe sources for the polypeptide factor of the invention, for investigating, isolating or preparing such a factor (or corresponding gene sequences) from a range of different species, or preparing the factor by recombinant technology, and in the generation of corresponding antibodies, by conventional technologies, preferably monoclonal antibodies, which are themselves useful investigative tools in relation to the present factor and are themselves candidate medicaments. Such antibodies are included within this invention. The invention also includes an isolated glial cell mitogenic activity encoding gene sequence, or fragment thereof, obtainable by the use set out above for the novel peptide sequences of the invention.

A further aspect of the invention is a polypeptide having glial cell mitogenic activity and reactive with an antibody directed against any one of the above novel peptide sequences or a polypeptide comprising any such sequence.

In another respect, the invention provides a polypeptide factor which has, if obtained from bovine pituitary material, an observed molecular weight (when carrying native glycosylation), under non-reducing conditions, of from about 43 kD to about 45 kD on SDS-polyacrylamide gel electrophoresis using the following molecular weight standards:

| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400; | which factor has mitogenic activity stimulating the division of rat Schwann cells.

For convenience of description only, a factor of this invention will sometimes be referred to hereinafter as "GGF-III".

It will be appreciated that the molecular weight range limits quoted are not exact, but are subject to slight variation depending, inter alia, upon the source of the particular polypeptide factor. A variation of, say, about 10% would not, for example, be impossible for material from another source.

The invention includes any modifications or equivalents of a polypeptide factor of the invention which do not exhibit a significantly reduced activity. For example, modifications in which amino acid content or sequence is altered without substantially adversely affecting activity are included. By way of illustration only, in EP-A-109748 muteins of native proteins are disclosed in which the possibility of unwanted —S—S— bonding is avoided by replacing any cysteine in the native sequence not necessary for biological activity with a neutral amino acid. The statements of effect and use contained herein are therefore to be construed accordingly, with such uses and effects employing a modified or equivalent factor as aforesaid being part of the invention. The invention also includes a polypeptide or peptide of the invention for use as a $p185^{erbB2}$ receptor ligand. Additionally, the invention includes the use of a polypeptide or peptide of the invention as a $p185^{erbB2}$ ligand, whether for prophylactic or therapeutic purposes, or otherwise. The invention also encompasses a method of prophylaxis or therapy involving either use of a polypeptide or peptide of the invention as a $p185^{erbB2}$ receptor ligand or inhibition of such ligand function.

Other important aspects of the invention are constituted by DNAs encoding polypeptides of the invention or any one of the above novel peptide sequences.

The invention also includes the following aspects:

(a) a DNA construct comprising a DNA as defined above in operable reading frame position in a vector under the control of a control sequence so as to permit expression in chosen host cells after transformation thereof by said construct (preferably said control sequence includes a regulatable promoter, e.g. Trp)—it will be appreciated that the selection of a promoter and regulatory sequences (if any) are matters of choice for those of skill in the art;

(b) host cells modified by incorporating a construct as defined in (a) immediately above so that said DNA may be expressed in said host cells—the choice of host is not critical, and chosen cells may be prokaryotic or eukaryotic and may be genetically modified to incorporate said construct by methods known in the art; and (c) a process for the preparation of a factor of the invention comprising cultivating said modified host cells under conditions permitting expression of an appropriate said DNA, which conditions can be readily determined, for any particular embodiment, by those of skill in the art of recombinant DNA technology. Glial cell mitogens prepared by this means are included in the present invention.

The Schwann cell assay described herein which can be used to characterise a factor of this invention employs a background of foetal calf plasma. In all other respects, the assay can by the same as that described by Brockes et al. in Meth. Enz., supra, but with 10% FCP replacing 10% FCS. This difference in assay technique is significant, since the absence of platelet-derived factors in foetal calf plasma (as opposed to serum) enables a more rigorous definition of activity on Schwann cells to be provided by eliminating potentially spurious effects from some other factors.

Yet a further aspect of the invention is a process for the preparation of a polypeptide as defined above, comprising extracting vertebrate brain material to obtain protein, subjecting the resulting extract to chromatographic purification comprising hydroxylapatite HPLC and thereafter to SDS-polyacrylamide gel electrophoresis and collecting that fraction therefrom which (when carrying native glycosylation) has an observed molecular weight of about 43 kD to 45 kD if subjected to SDS-polyacrylamide gel electrophoresis (under non-reducing conditions) using the following molecular weight standards:

| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400; | and which fraction exhibits activity stimulating the division of rat Schwann cells.

Preferably, the above process starts by isolating a relevant fraction obtained by carboxymethyl cellulose chromatography, eg from bovine pituitary material. It is also preferred that after hydroxylapatite HPLC, cation exchange chromatography, gel filtration, and/or reversed-phase HPLC be employed prior to the SDS-Polyacrylamide gel electrophoresis. At each stage in the process, activity may be determined using Schwann cell incorporation of radioactive iododeoxyuridine as a measure in an assay generally as described by Brockes in Meth. Enz., supra, but modified by substituting 10% FCP for 10% FCS.

Another aspect of the invention is a pharmaceutical or veterinary formulation comprising a factor as defined above formulated for pharmaceutical or veterinary use, respectively, optionally together with an acceptable diluent, carrier or excipient and/or in unit dosage form. In using the factors of the invention, conventional pharmaceutical or veterinary practice may be employed to provide suitable formulations or compositions.

Thus, the formulations of this invention can be applied to parenteral administration, for example, intravenous, subcutaneous, intramuscular, intraorbital, ophthalmic, intraventricular, intracranial, intracapsular, intraspinal, intracisternal, intraperitoneal, topical, intranasal, aerosol, scarification, and also oral, buccal, rectal or vaginal administration.

The formulations of this invention may also be administered by the transplantation into the patient of host cells expressing the DNA of the instant invention or by the use of surgical implants which release the formulations of the invention.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain as excipients sterile water or saline, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

A factor of the invention can be used as the sole active agent or can be used in combination with other active ingredients, eg, other growth factors which could facilitate neuronal survival in neurological diseases, or peptidase or protease inhibitors.

The concentration of the factor of the invention in the formulations of the invention will vary depending upon a number of issues, including the dosage to be administered, and the route of administration.

In general terms, a factor of this invention may be provided in an aqueous physiological buffer solution containing about 0.1 to 10% w/v compound for parenteral administration. General dose ranges are from about 1 µg/kg to about 1 g/kg of body weight per day; a preferred dose range is from about 0.01 mg/kg to 100 mg/kg of body weight per day. The preferred dosage to be administered is likely to depend upon the type and extent of progression of the pathophysiological condition being addressed, the overall health of the patient, the make up of the formulation, and the route of administration.

As indicated above, Schwann cells (the glial cells of the peripheral nervous system) are stimulated to divide in the presence of a factor of the invention. Schwann cells of the peripheral nervous system are involved in creating the myelin sheath around individual nerve fibres which is important for proper conduction of electrical impulses to muscles and from sensory receptors.

There are a variety of peripheral neuropathies in which Schwann cells and nerve fibres are damaged, either primarily or secondarily. There are many neuropathies of both sensory and motor fibres (Adams and Victor, Principles of Neurology). The most important of those neuropathies are probably multiple sclerosis, the neuropathies associated with diabetes, Landry-Guillain-Barre syndrome, neuropathies caused by carcinomas, and neuropathies caused by toxic agents (some of which are used to treat carcinomas).

The invention, however, envisages treatment or prophylaxis of conditions where nervous system damage has been brought about by any basic cause, eg infection or injury. Thus, in addition to use of a factor of the invention in the treatment of disorders or diseases of the nervous system where demyelination or loss of Schwann cells is present, such a glial growth factor can be valuable in the treatment of disorders of the nervous system that have been caused by damage to the peripheral nerves. Following damage to peripheral nerves, the regeneration process is led by the growth or the re-establishment of Schwann cells, followed by the advancement of the nerve fibre back to its target. By speeding up the division of Schwann cells one could promote the regenerative process following damage.

Furthermore, there are a variety of tumours of glial cells, or of tissues which either at some point include glial cells or can in some other way be said to be influenced by glial cells. For example, neurofibromatosis is a patchy small tumour created by overgrowth of glial cells. Also, it has been found that an activity very much like GGF can be found in some Schwann cell tumours, and therefore inhibitors of the action of factors of the invention on their receptor provides a therapy for tumours. The invention thus specifically includes a method for the prophylaxis or treatment of a glial cell tumour or glial cell-influenced tumour, which comprises administering an effective amount of a substance which inhibits the binding of a factor as defined above to a receptor therefor.

In general, the invention includes the use of a polypeptide factor of the invention in the prophylaxis or treatment of any pathophysiological condition, eg of the nervous system, in which a factor-sensitive or factor-responsive cell type is involved.

A polypeptide factor of the invention can also be used as an immunogen for making antibodies, such as monoclonal antibodies, following standard techniques. Such antibodies are included within the present invention. These antibodies can, in turn, be used for diagnostic purposes. Thus, conditions perhaps associated with abnormal levels of the factor may be tracked by using such antibodies. In vitro techniques can be used, employing assays on isolated samples using standard methods. Imaging methods can also be employed in which the antibodies are, for example, tagged with radioactive isotopes which can be imaged outside the body using techniques employed in the art of, for example, tumour imaging.

The invention also includes the general use of a factor of the invention as a glial cell mitogen in vivo or in vitro, and such a factor for such use. One specific embodiment is thus a method for producing a glial cell mitogenic effect in a vertebrate by administering an effective amount of a factor of the invention. A preferred embodiment is such a method in the treatment or prophylaxis of a nervous system disease or disorder, eg multiple sclerosis.

A further general aspect of the invention is the use of a factor of the invention in the manufacture of a medicament, preferably for the treatment of a nervous disease or disorder or for neural regeneration or repair.

Also included in the invention are the use of a factor of the invention in competitive assays to identify or quantify molecules having receptor binding characteristics corresponding to those of said polypeptide factor. The polypeptide may be labelled, optionally with a radioisotope. A competitive assay can identify both antagonists and agonists of the relevant receptor.

In another aspect, the invention provides the use of a factor of the invention in an affinity isolation process, optionally affinity chromatography, for the separation of a respective corresponding receptor. Such processes for the isolation of receptors corresponding to particular proteins are known in the art, and a number of techniques are available and can be applied to the factor of the present invention. For example, in relation to IL-6 and IFN-gamma the reader is referred to Novick, D. et al., J. Chromatogr.; 1990, June 27; 510, 331–7, in relation to gonadotropin releasing hormone reference is made to Hazum, E., J. Chromatogr.; 1990, June 27; 510, 233–8, in relation to G-CSF reference is made to Fukunaga, R., et al., J. Biol. Chem.; 1990, Aug. 15; 265(23), 14008–15, in relation to vasoactive intestinal peptide reference is made to Couvineau, A., et al., J. Biol. Chem.; 1990, Aug. 5; 265(22), 13386–90, in relation to IL-2 reference is made to Smart, J. E., et al., J. Invest. Dermatol.; 1990, June; 94(6 Suppl.), 158S–163S, and in relation to human IFN-gamma reference is made to Stefanos, S., et al., J. Interferon Res.; 1989, Dec., 9(6), 719–30.

The following Example is not intended to limit the invention, but usefully illustrates the same, and provides specific guidance for effective preparative techniques.

In the Example hereinafter, unless otherwise indicated, all operations were conducted at 4° C., and, with reference to FIGS. 1 to 5, activity at each stage was determined using the Brockes (Meth. Enz., supra) techniques with the following modifications. Thus, in preparing Schwann cells, 5 μM forskolin was added in addition to DMEM (Dulbecco's modified Eagle's medium), FCS and the factor for testing. Cells used in the assay were fibroblast-free Schwann cells at passage number less than 10, and these cells were removed from flasks with trypsin and plated into flat-bottomed 96-well plates at 3.3 thousand cells per microwell. [$^{125}$I] IUdR was added for the final 24 hours after the test solution addition. The background (unstimulated) incorporation to each assay was less than 100 cpm, and maximal incorporation was 20 to 200 fold over background depending on Schwann cell batch and passage number.

Figure 8:
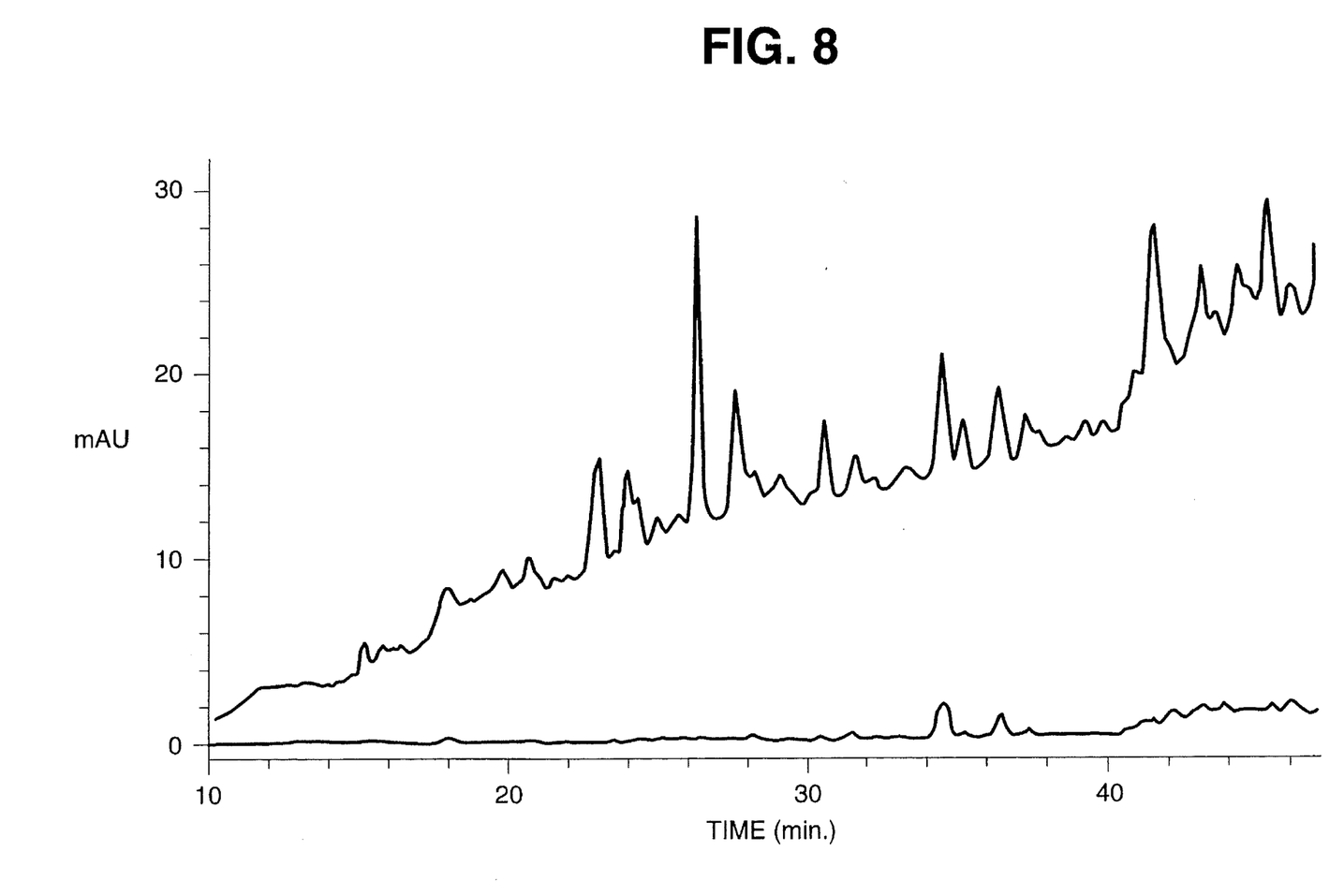
FIG. 8 is the absorbance profile (240 nm) of GGF-III peptides produced by lysylendopeptidase digestion of SDS PAGE purified material, eluted from a C18 reversed-phase column.
Figure 9:
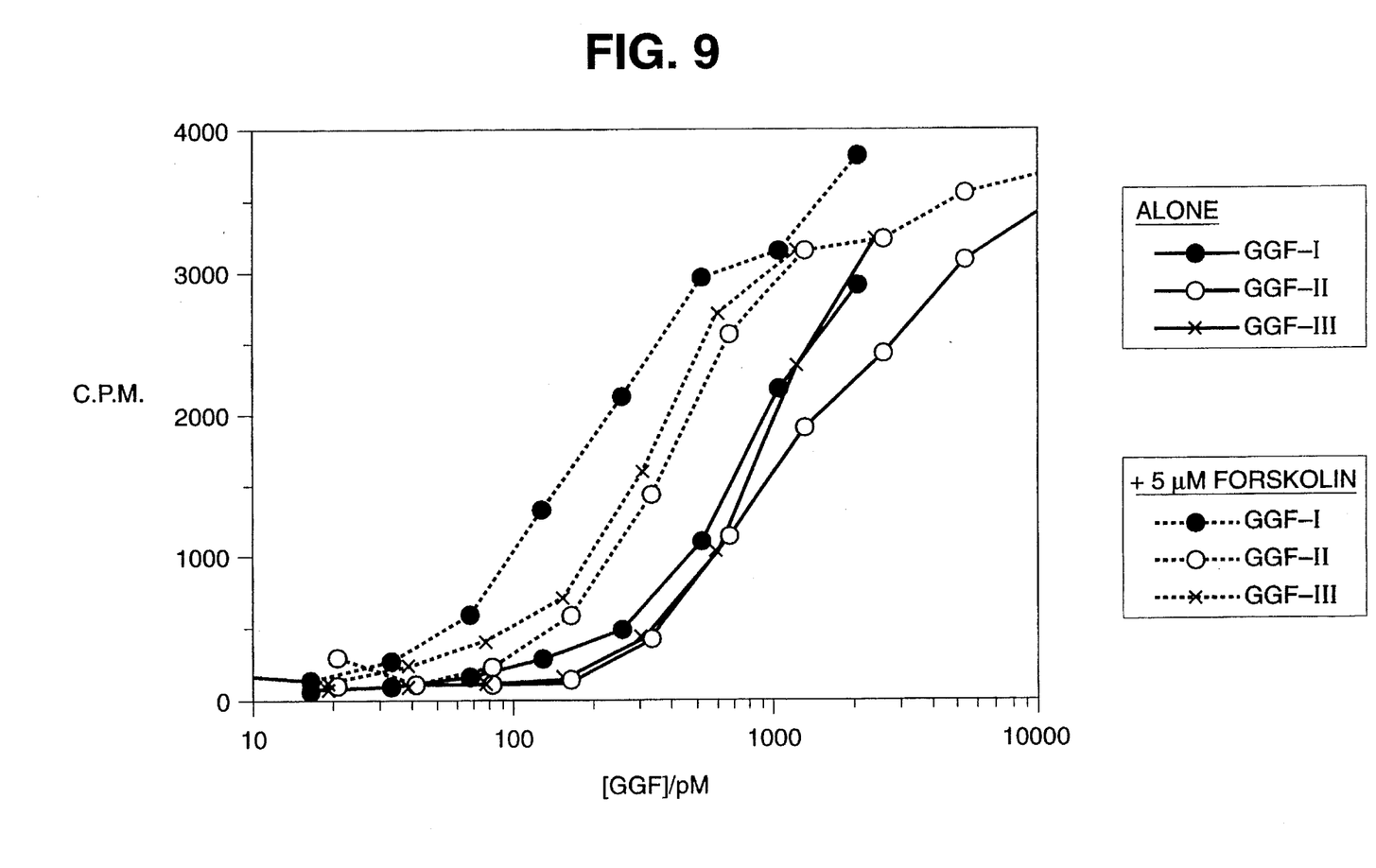
FIG. 9 shows the response of Schwann cells to various factors, including GGF-III, and forskolin.

Dose response curves were also produced for the factor of this using, firstly, exactly the above method for each factor but leaving out forskolin, and, secondly, exactly the above method. The results are in FIG. 8.

EXAMPLE

In carrying out the following, the initial stages follow the procedure described in copending PCT Application No PCT/GB92/00595 directed to the preparation of factors known as GGF-I and GGF-II.

(A) Preparation of Factor-CM Fraction 4,000 frozen whole bovine pituitaries (c.a. 12 kg) were thawed overnight, washed briefly with water and then homogenised in an equal volume of 0.15M ammonium sulphate in batches in a Waring Blender. The homogenate was taken to pH 4.5 with 1.0M HCl and centrifuged at 4,900 g for 80 minutes. Any fatty material in the supernatant was removed by passing it through glass wool. After taking the pH of the supernatant to 6.5 using 1.0M NaOH, solid ammonium sulphate was added to give a 36% saturated solution. After several hours stirring, the suspension was centrifuged at 4,900 g for 80 minutes and the precipitate discarded. After filtration through glass wool, further solid ammonium sulphate was added to the supernatant to give a 75% saturated solution which was once again centrifuged at 4,900 g for 80 minutes after several hours stirring. The pellet was resuspended in c.a. 2 L of 0.1 M sodium phosphate pH 6.0 and dialysed 3×40 L of the same buffer. After confirming that the conductivity of the dialysate was below 20.0 mSiemens, it was loaded on to a Bioprocess column (120×113 mm, Pharmacia) packed with carboxymethyl cellulose (CM-52, Whatman) at a flow rate of 2 ml.min$^{-1}$.

The column was washed with 2 volumes of 0.1M sodium phosphate pH 6.0, followed by 2 volumes of 50 mM NaCl, and finally 2 volumes of 0.2M NaCl both in the same buffer. During the final step, 10 mL (5 minute) fractions were collected. Fractions 73 to 118 inclusive were pooled, dialysed against the 10 volumes of 10 mM sodium phosphate pH 6.0 twice and clarified by centrifugation at 100,000 g for 60 minutes.

(B) Hydroxylapatite HPLC

Hydroxylapatite HPLC is not a technique hitherto used in isolating glial growth factors, but proved particularly efficacious in this invention.

The material obtained from the above CM-cellulose chromatography was filtered through a 0.22 um filter (Nalgene), loaded at room temperature on to a high performance hydroxylapatite column (50×50 mm, Biorad) equipped with a guard column (15×25 mm, Biorad) and equilibrated with 10 mM potassium phosphate pH 6.0. Elution at room temperature was carried out at a flow rate of 2 mL.minute$^{-1}$ using the following programmed linear gradient:

| time (min) | % B | Solvent A: 10 Mm potassium phosphate pH 6.0 |
|---|---|---|
| 0.0 | 0 | Solvent B: 1.0M potassium phosphate pH 6.0 |
| 5.0 | 0 | |
| 7.0 | 20 | |
| 70.0 | 20 | |
| 150.0 | 100 | |
| 180.0 | 100 | |
| 185.0 | 0 | |

6.0 mL (3 minutes) fractions were collected during the gradient elution. Fractions 39–45 were pooled and dialysed against 10 volumes of 50 mM sodium phosphate pH 6.0.

(C) Mono S FPLC

Mono S FPLC enabled a more concentrated material to be prepared for subsequent gel filtration.

Any particulate material in the pooled material from the hydroxylapatite column was removed by a clarifying spin at 100,000 g for 60 minutes prior to loading on to a preparative HR10/10 Mono S cation exchange column (100×10 mm, Pharmacia) which was then re-equilibrated to 50 mM sodium phosphate pH 6.0 at room temperature with a flow rate of 1.0 mL.minute$^{-1}$. Under these conditions, bound protein was eluted using the following programmed linear gradient:

| time (min) | % B | Solvent A: 50 mM potassium phosphate pH 6.0 |
|---|---|---|
| 0.0 | 0 | Solvent B: 1.2M sodium chloride, 50 mM |
| 70.0 | 30 | sodium phosphate pH 6.0 |
| 240.0 | 100 | |
| 250.0 | 100 | |
| 260.0 | 0 | |

1 mL (1 minute) fractions were collected throughout this gradient programme. Fractions 99 to 115 inclusive were pooled.

(D) Gel Filtration FPLC

This step commenced the separation of the two factors GGF-I and GGF-II, as well as GGF-III, prior to final purification, producing enriched fractions.

For the purposes of this step, a preparative Superose 12 FPLC column (510×20 mm, Pharmacia) was packed according to the manufacturers' instructions. In order to standardize this column, a theoretical plates measurement was made according to the manufacture's instructions, giving a value of 9,700 theoretical plates.

The pool of Mono S eluted material was applied at room temperature in 2.5 mL aliquots to this column in 50 mM sodium phosphate, 0.75 NaCl pH 6.0 (previously passed through a C18 reversed phase column (Sep-pak, Millipore)) at a flow rate of 1.0 mL.minute$^{-1}$. 1 mL (0.5 minute) fractions were collected from 35 minutes after each sample was applied to the column. Fractions 27 to 41 (GGF-II) and 42 to 57 (GGF-I) inclusive from each run were pooled.

(E) Reversed-Phase HPLC

The "GGF-I" and "GGF-II" pools from the above Superose 12 runs were each divided into three equal aliquots. Each aliquot was loaded on to a C8 reversed-phase column (Aquapore RP-300 7μ C8 220×4.6 mm, Applied Biosystems) protected by a guard cartridge (RP-8, 15×3.2 mm, Applied Biosystems) and equilibrated to 40° C. at 0.5 mL.minute$^{-1}$. Protein was eluted under these conditions using the following programmed linear gradient:

| time (min) | % B | Solvent A: 0.1% trifluoroacetic acid (TFA) |
|---|---|---|
| 0 | 0 | Solvent B: 90% acetonitrile, 0.1% TFA |
| 60 | 66.6 | |
| 62.0 | 100 | |
| 72.0 | 100 | |
| 75.0 | 0 | |

200 μL (0.4 minute) fractions were collected in siliconised tubes (Multilube tubes, Bioquote) from 15.2 minutes after the beginning of the programmed gradient.

Figure 1:
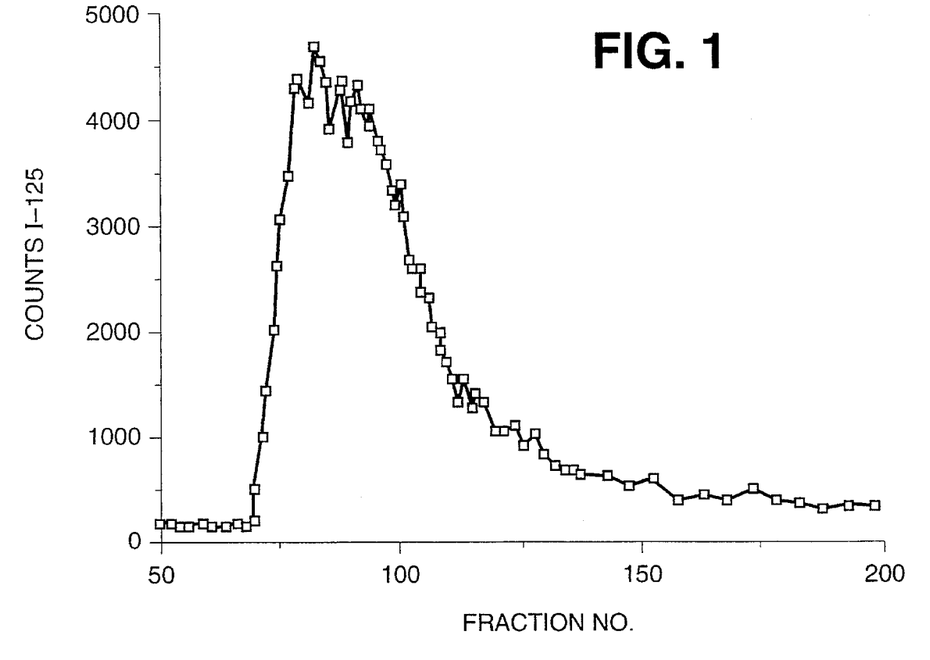
FIG. 1 is the profile for product from carboxymethyl cellulose chromatography.
Figure 2:
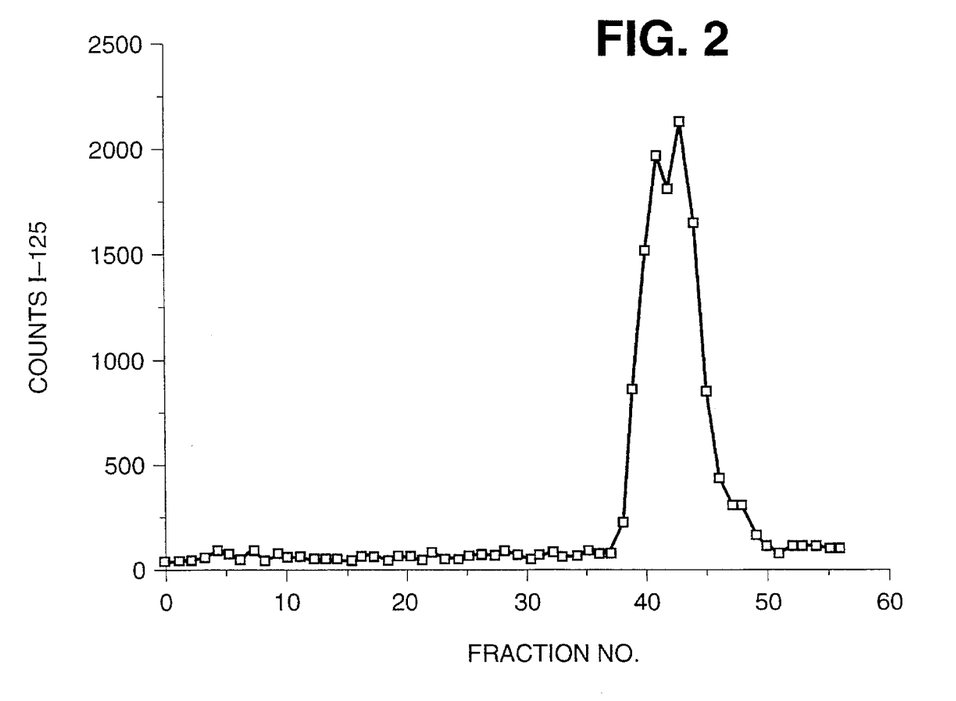
FIG. 2 is the profile for product from hydroxylapatite HPLC.
Figure 3:
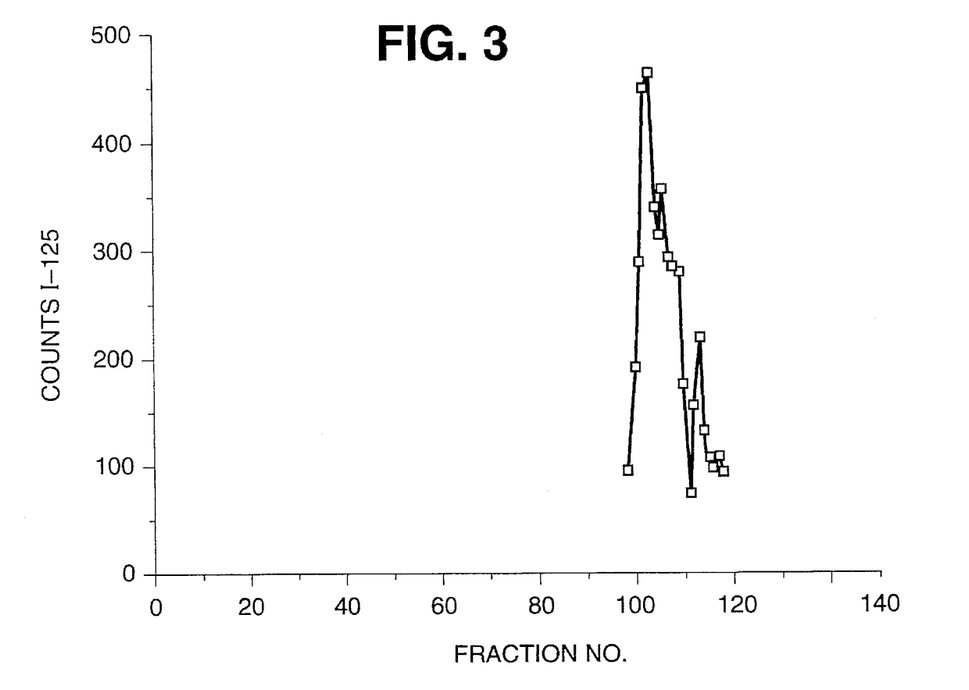
FIG. 3 is the profile for product from Mono S FPLC.
Figure 4:
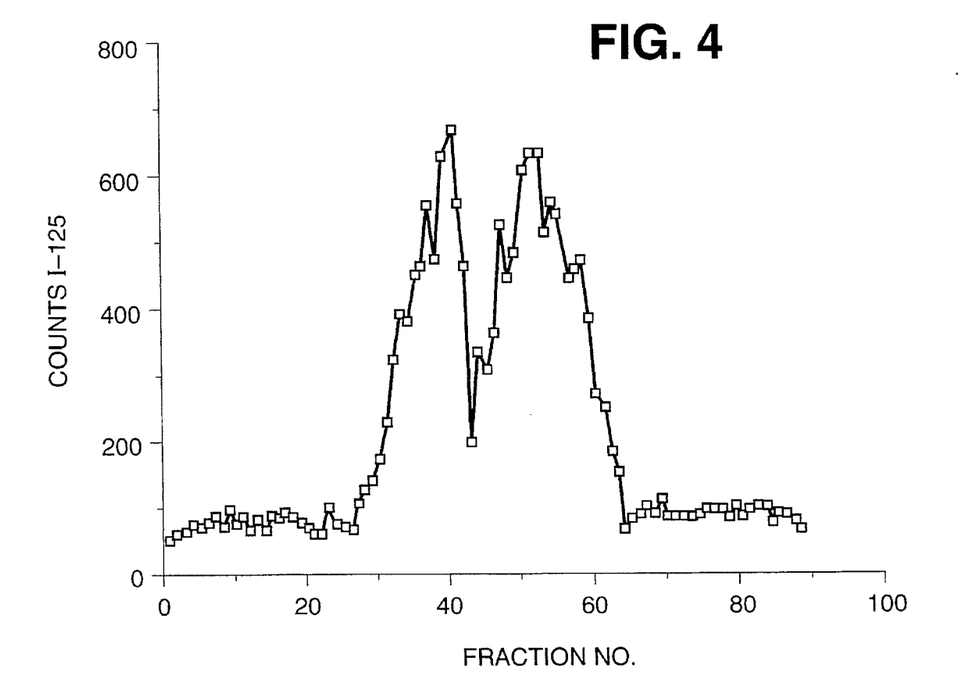
FIG. 4 is the profile for product from Gel filtration FPLC.
Figure 5:
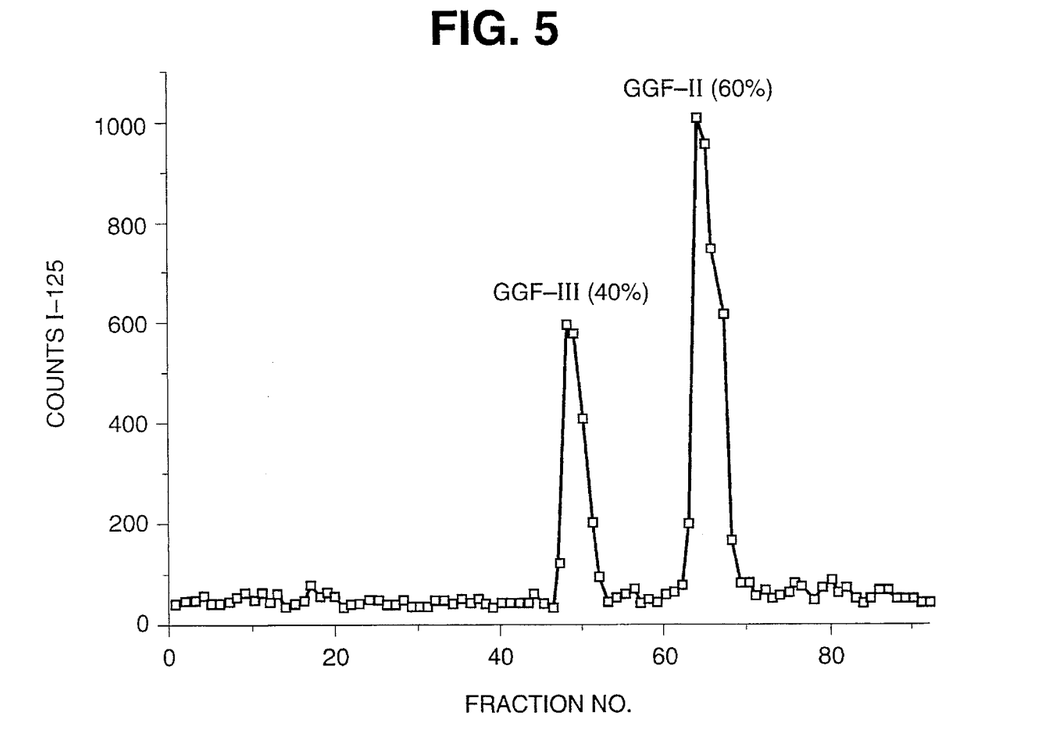
FIG. 5 shows elution of the "60K" glial cell mitogenic activity from gel filtration FPLC from a C8 reversed phase HPLC column showing activity plotted against fraction number.

GGF-like activity elutes from the Superose 12 gel filtration column used in (D) above in two overlapping peaks centred at molecular weights of about 30 kD and ca 60 kD (FIG. 4). The former peak yields predominantly a single species on the above reversed phase HPLC, GGF-I. But, as can be seen from FIG. 5, the 60 kD peak yields two peaks on the above reversed phase HPLC, with 60% of the GGF-like activity eluting as GGF-II and the remaining 40% having reversed phase characteristics that are indistinguishable from GGF-I.

(F) SDS-Polyacrylamide Gel Electrophoresis

In this step, protein molecular weight standards, low range, catalogue no. 161-0304, from Bio-Rad Laboratories Limited, Watford, England were employed. The actual proteins used, and their molecular weight standards, have been listed hereinbefore.

Fractions 47 to 53 (elution position for GGF-I) and fractions 61 to 67 (GGF-II) inclusive from the reversed-phase runs were individually pooled. 7 μL of the pooled material was boiled in an equal volume of 0.0125M Tris-Cl 4% SDS, 20% glycerol, and 10% β-mercaptoethanol for GGF-I, for 5 minutes and loaded on to an 11% polyacrylamide Leammli gel with a 4% stacking gel and run at a constant voltage of 50 V for 16 hours. This gel was then fixed and stained using a silver staining kit (Amersham). Under these conditions, the factors GGF-I and GGF-II are each seen as a somewhat diffuse band at relative molecular weights 30,000 to 36,000 Daltons (GGF-I) and 55,000 to 63,000 Daltons (GGF-II) as defined by molecular weight markers.

Figure 6:
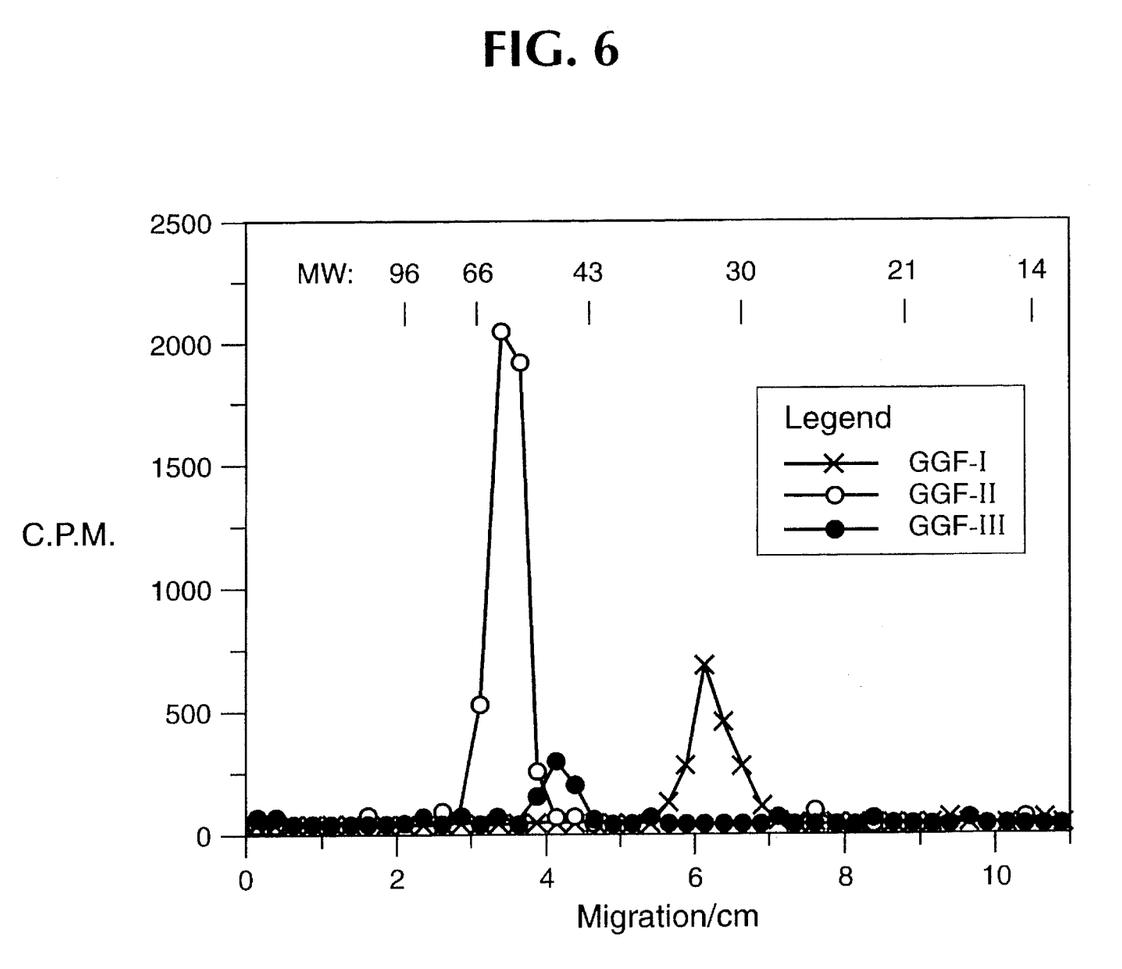
FIG. 6 shows elution of glial cell mitogenic activity after SDS-PAGE under non-denaturing conditions. Activity is plotted against the migration distance from the top of the electrophoretic gel. The GGF-III sample was a pool of fractions 48–50 from the reversed phase HPLC run.
Figure 7:
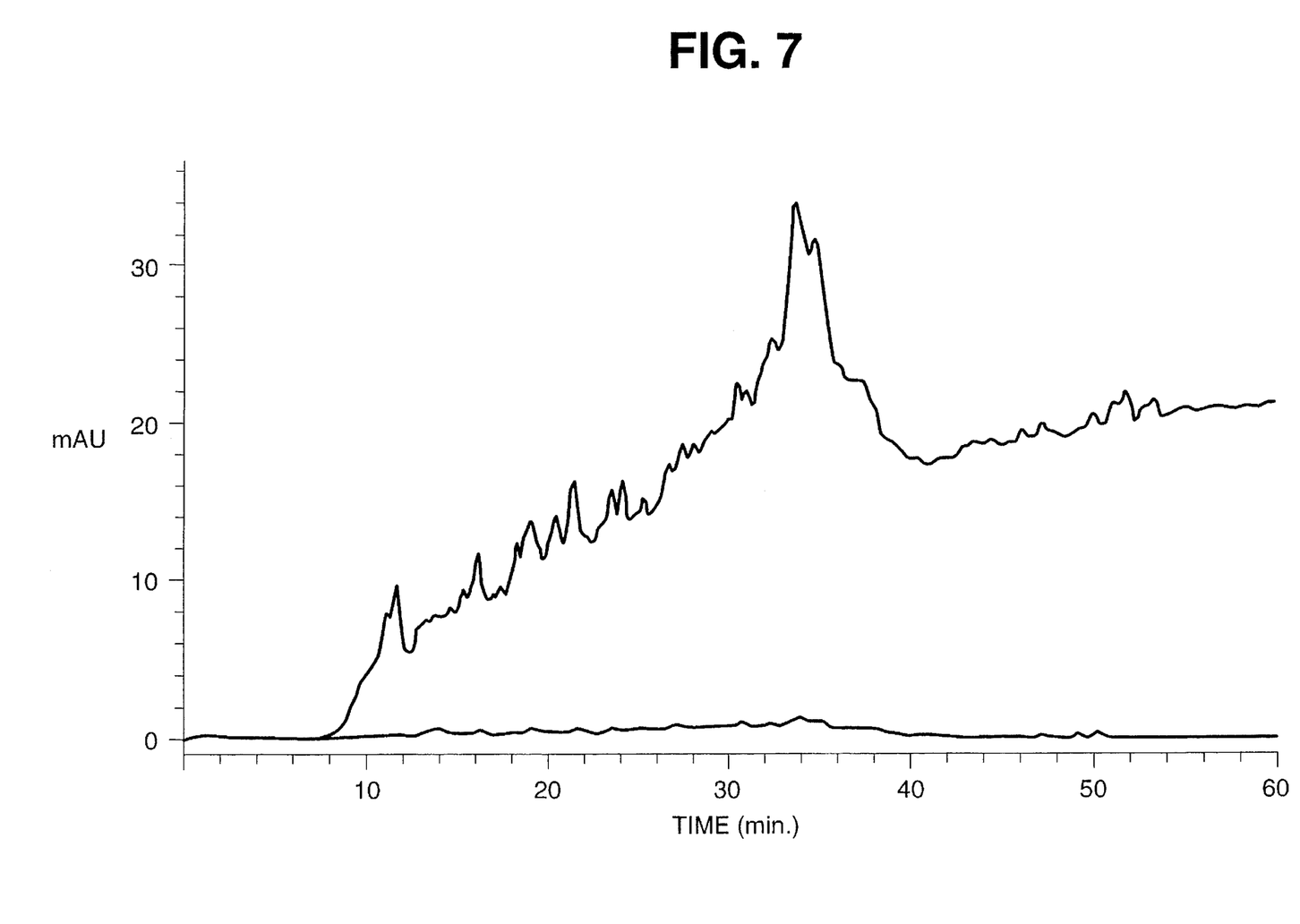
FIG. 7 is the absorbance profile (214 nm) of GGF-III peptides produced by tryptic digestion, eluted from a C18 reversed phase HPLC column.

However, SDS-PAGE of fractions across the reversed phase HPLC peak responsible for 40% of the GGF-like activity derived from the 60 kD Superose gel filtration peak (see (E) above) revealed no staining in the 32–34 kD region. Instead, somewhat diffuse silver staining was seen at a molecular weight of 43–45 kD whose intensity correlates well with the amount of GGF activity present in each fraction. The mobility of this species on SDS-PAGE increased slightly across the reversed phase peak. Elution of activity from electrophoretic gels run in the absence of reducing agents confirmed the assignment of GGF activity to the 43–45 kD band, and that no GGF-I or GGF-II was present in these fractions (FIG. 6). This novel activity was named GGF-III.

In the above SDS-PAGE, elution of activity from electrophoretic gels was carried out according to the following protocol:

1. Before removing the comb from the stacking gel, mark the position of the bottom of each well on both gel plates with a fine marker pen and number each lane.
2. When the gel has been run, mark the outer limits of each lane with two parallel lines down each plate.
3. Open up plates, ensuring that the whole of the separating gel sticks to one of the plates. Clear stacking gel out of the way by cutting along stacker/separator interface and scraping stacker away.

4. Using a new scalpel blade, cut the gel along the parallel lines and remove the gel pieces outside the lanes. Put them to fix/stain/destain so as to calibrate the gel by the positions of the stained standards.

5. Place gel over a sheet of graph paper with cm squares. Make a note of the length of the separating gel for calibration correction later.

6. Cut 0.25 cm slices horizontally in lanes; then place pieces in 1 ml "Micronic" tubes.

7. When all slices are in the tubes, add 0.5 ml of 10 mg/ml BSA in PBS (w/o calcium, magnesium or sodium bicarbonate) per tube, put caps on tubes and agitate on vibrator (Luckham, Model 804) (setting 7) for 1 hour.

8. Aspirate gently and wash with 0.5 ml BSA/PBS.

9. Aspirate gently and then, in the vertical flow hood, add 50 µl of 0.2 µm filtered BSA/PBS, put caps on tubes and leave on vibrator overnight.

10. Assay 10 µl in duplicate in Schwann cell proliferation assay.

11. Measure length of fixed/stained/destained gel and positions of the standards. This gel usually expands by about 10% relative to the unstained gel so the migration distances of the standards must be multiplied by the ratio of the unstained vs stained gel lengths for comparison with activity peaks in the gel slices.

(G) Amino Acid Sequence Analysis

Sequence analysis studies were performed using purified bovine pituitary GGF-III.

1. Trypsin Digest

Peptides were obtained by a tryptic digest using material from the final reversed-phase column run. The resulting peptides were separated by reversed-phase HPLC. Sequences obtained were:

Lys-Ile-Ser-Lys-Pro-Asp-Leu-Lys-Pro-Phe-Thr-X-Glu-Val-X-(Lys)
Leu-Leu-Gln-Ala-Gln-Gly-Val-Glu-Val-Pro-Ser-Lys-Asp-Ser
Ala-Ser-Glu-Tyr-Ala-Phe-Phe-Glu-Gln-Thr-X-Arg-Glu
Ala-Pro-Pro-Ser-Ala-Phe-Phe-Leu-Phe
Tyr-Glu-Lys-Asp-Ile-Ala-Ala-Tyr-Lys
Lys-Pro-Arg-Asp-Ser-Gln-Ala-Gln-Tyr-Ala-Ala-Glu-Lys
Leu-Leu-Glu-Met-Ala-X-Glu-Val-Lys
Ile-Lys-Gly-Glu-His-Pro-Gly-Leu-Ser-Ile-Gly-Asp-Val-Ala-Lys
(Lys)-Leu-Ala-Thr-Gly-Ala-Val-Pro-Ala-Ser-Leu-Lys

X denotes an unassigned residue. The last five of the above-listed peptides were sequenced to completion. None of these sequences is apparently related to GGF-I or GGFII peptide sequences.

2. Gel-Purified Lyslylendopeptidase Digest

Peptides were obtained by a lysylendopeptidase digest using material from the final reversed-phase column run separated on a material from the final reversed-phase column run separated on a 12% SDS PAGE gel. The position of the GGF-III was identified following staining with Coomassie R250, and the visible band in the 43–45 kD region of the gel excised (molecular weight as originally defined relative to the above-quoted markers). After washing the excised gel piece and in situ digestion with lyslyendopeptidase, the peptides were extracted by passive washing and separated by reversed-phase HPLC. Since these peptides originated solely from the region of the gel in which activity is found, they do not contain other potential contaminant proteins.

Lys-Ser-Glu-Leu-Arg-Ile-Ser-Lys
Lys-Leu-Gly-Asn-Asp-Ser-Ala-Ser-Ala-Asn-Ile-Thr-Ile-Val
Lys-Ala-Ser-Leu-Ala-Asp-Ser-Gly-Glu-Tyr-Met-X-Lys
Lys-Trp-Phe-Lys
Lys-Asp-Leu-Ser-Asn-Pro-Ser-Arg-Tyr-Leu-X-Lys (H) N-Glycanase Treatment This was carried out on GGF-III according to the manufacturers instructions:

1. GGF-III samples were dried down under vacuum, resuspended in 100 µl of water, and dried down under vacuum once again.

2. Samples were then resuspended in 10 µl 10.25% SDS and boiled for 5 minutes. (For samples destined to be analysed by silver stained SDS-PAGE, 100 mM β-mercaptoethanol was included).

3. Buffers were added to give a final concentration of 100 mM sodium phosphate pH 8, 10 mM EDTA, 1% NP-40 in a total volume of 28.8 µl.

4. 1.2 µl of N-Glycanase (=treated) or water (=native) was added and samples incubated at 37° overnight (=16–18 hours). Samples were then run on SDS-PAGE and analysed by silver staining or activity elution as described in (F) above.

Silver staining shows that there is only a very slight shift in mobility of GGF-III upon N-glycanase treatment, shifting molecular weight by only 1–2 kD indicating relatively little native glycosylation.

We claim:

1. Purified glial growth factor-III having mitogenic activity stimulating the division of Schwann cells, and exhibiting a molecular weight of from about 43 kD to about 45 kD when carrying native glycosylation when assessed on SDS PAGE.

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 16 amino acids
        ( B ) TYPE: amino acids
        ( D ) TOPOLOGY: linear     ( i i ) MOLECULE TYPE: protein     ( x i ) SEQUENCE DESCRIPTION: SEQ ID NO: 1:

Lys   Ile   Ser   Lys   Pro   Asp   Leu   Lys   Pro   Phe   Thr   Xaa   Glu   Val   Xaa   Lys
                      5                                10

( 2 ) INFORMATION FOR SEQ ID NO: 2:

( i ) SEQUENCE CHARACTERISTICS:
        ( A ) LENGTH: 14 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 2:

Leu Leu Gln Ala Gln Gly Val Glu Val Pro Ser Lys Asp Ser
            5                        10

( 2 ) INFORMATION FOR SEQ ID NO: 3:

( i ) SEQUENCE CHARACTERISTICS:
        ( A ) LENGTH: 13 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 3:

Ala Ser Glu Tyr Ala Phe Phe Glu Gln Thr Xaa Arg Glu
            5                      10

( 2 ) INFORMATION FOR SEQ ID NO: 4:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 4:

Ala Pro Pro Ser Ala Phe Phe Leu Phe
            5

( 2 ) INFORMATION FOR SEQ ID NO: 5:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 5:

Tyr Glu Lys Asp Ile Ala Ala Tyr Lys
            5

( 2 ) INFORMATION FOR SEQ ID NO: 6:

( i ) SEQUENCE CHARACTERISTICS:
        ( A ) LENGTH: 13 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 6:

Lys Pro Arg Asp Ser Gln Ala Gln Tyr Ala Ala Glu Lys
            5                      10

( 2 ) INFORMATION FOR SEQ ID NO: 7:

( i ) SEQUENCE CHARACTERISTICS:
        ( A ) LENGTH: 9 amino acids
        ( B ) TYPE: amino acid ( D ) TOPOLOGY: linear ( i i ) MOLECULE TYPE: protein ( x i ) SEQUENCE DESCRIPTION: SEQ ID NO: 7:

Leu Leu Glu Met Ala Xaa Glu Val Lys
                  5

( 2 ) INFORMATION FOR SEQ ID NO: 8:

( i ) SEQUENCE CHARACTERISTICS:
        ( A ) LENGTH: 15 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 8:

Ile Lys Gly Glu His Pro Gly Leu Ser Ile Gly Asp Val Ala Lys
                  5                   1 0                  1 5

( 2 ) INFORMATION FOR SEQ ID NO: 9:

( i ) SEQUENCE CHARACTERISTICS:
        ( A ) LENGTH: 12 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 9:

Lys Leu Ala Thr Gly Ala Val Pro Ala Ser Leu Lys
                  5                   1 0

( 2 ) INFORMATION FOR SEQ ID NO: 10:

( i ) SEQUENCE CHARACTERISTICS:
        ( A ) LENGTH: 8 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 10:

Lys Ser Glu Leu Arg Ile Ser Lys
                  5

( 2 ) INFORMATION FOR SEQ ID NO: 11:

( i ) SEQUENCE CHARACTERISTICS:
        ( A ) LENGTH: 14 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 11:

Lys Leu Gly Asn Asp Ser Ala Ser Ala Asn Ile Thr Ile Val
                  5                   1 0

( 2 ) INFORMATION FOR SEQ ID NO: 12:

( i ) SEQUENCE CHARACTERISTICS:
        ( A ) LENGTH: 13 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 12:

```
Lys Ala Ser Leu Ala Asp Ser Gly Glu Tyr Met Xaa Lys
                 5                      10
```

( 2 ) INFORMATION FOR SEQ ID NO: 13:

( i ) SEQUENCE CHARACTERISTICS:
       ( A ) LENGTH: 4 amino acids
       ( B ) TYPE: amino acid
       ( D ) TOPOLOGY: linear ( i i ) MOLECULE TYPE: protein ( x i ) SEQUENCE DESCRIPTION: SEQ ID NO: 13:

```
Lys Trp Phe Lys
```

( 2 ) INFORMATION FOR SEQ ID NO: 14:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: protein ( x i ) SEQUENCE DESCRIPTION: SEQ ID NO: 14:

```
Lys Asp Leu Ser Asn Pro Ser Arg Tyr Leu Xaa Lys
                 5                      10
```